US00PP18756P2

(12) United States Plant Patent
Ren

(10) Patent No.: US PP18,756 P2
(45) Date of Patent: Apr. 22, 2008

(54) ***CALIBRACHOA* PLANT NAMED 'BALCABLITPI'**

(50) Latin Name: *Calibrachoa×hybrida*
Varietal Denomination: Balcablitpi

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/602,622

(22) Filed: Nov. 20, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Calibrachoa* plant named 'Balcablitpi', characterized by its light pink-colored flowers, medium green-colored foliage, and moderately vigorous, mounded-trailing growth habit.

1 Drawing Sheet

Latin name of genus and species of plant claimed: *Calibrachoa×hybrida.*

Variety denomination: 'Balcablitpi'.

BACKGROUND OF THE INVENTION

The present invention relates to a new and distinct cultivar of *Calibrachoa* plant botanically known as *Calibrachoa×hybrida* and hereinafter referred to by the cultivar name 'Balcablitpi'.

The new cultivar originated in a controlled breeding program in Elburn, Ill. during December 2003. The objective of the breeding program was the development of *Calibrachoa* cultivars with attractive flower coloration, medium green-colored foliage, and a moderately vigorous, mounted-trailing growth habit.

The new *Calibrachoa* cultivar is the result of cross-pollination. The female (seed) parent of the new cultivar is the proprietary *Calibrachoa×hybrida* breeding selection designated 2087-1, not patented, characterized by its medium pink-colored flowers, medium green-colored foliage, and mounded, trailing growth habit. The male (pollen) parent of the new cultivar is the proprietary *Calibrachoa×hybrida* breeding selection designated 2080-1A, not patented, characterized by its very light pink-colored flowers, dark green-colored foliage, and trailing growth habit. The new cultivar was discovered and selected as a single flowering plant within the progeny of the above stated cross-pollination during August 2004 in a controlled environment at Elburn, Ill.

Asexual reproduction of the new cultivar by terminal stem cuttings since August 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcablitpi' as a new and distinct cultivar of *Calibrachoa* plant:

1. Light pink-colored flowers;
2. Medium green-colored foliage; and

3. Moderately vigorous, mounded-trailing growth habit.

Plants of the new cultivar differ from plants of the female parent primarily in flower color and from plants of the male parent primarily in flower color, foliage color, and growth habit.

Of the many commercially available *Calibrachoa* cultivars known to the inventor, the most similar in comparison to the new cultivar is MINIFAMOUS Dark Pink+Eye 'KLECA04088', not patented. However, in side by side comparisons, plants of the new cultivar differ from plants of 'KLECA04088' in the following characteristics:

1. Plants of the new cultivar are narrower than plants of 'KLECA04088';
2. Plants of the new cultivar have smaller flowers than plants of 'KLECA04088'; and
3. Plants of the new cultivar have a flower color different from plants of 'KLECA04088'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcablitpi'. The plants were grown in 4.5 inch pots for 16 weeks in a greenhouse at West Chicago, Ill.

DETAILED BOTANICAL DESCRIPTION

Figure 1:
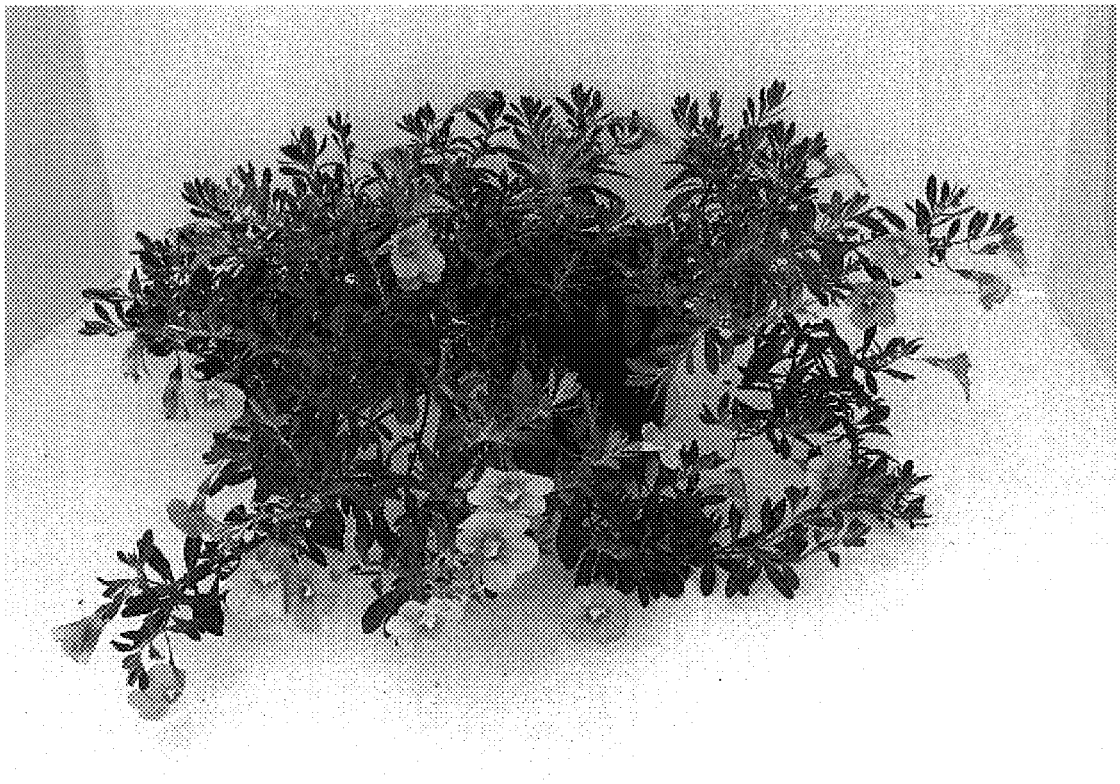
FIG. 1 illustrates a side view of the overall growth and flowering habit of 'Balcablitpi'.
Figure 2:
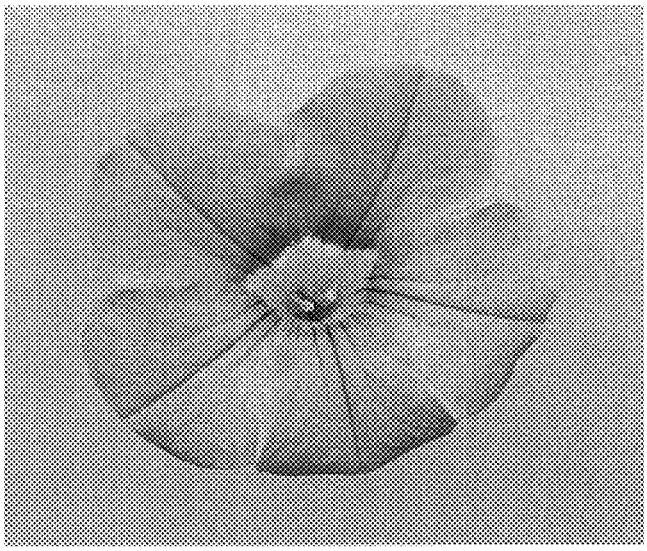
FIG. 2 illustrates a close-up view of an individual flower of 'Balcablitpi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 23, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 16 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Calibrachoa×hybrida* cultivar Balcablitpi.

Parentage:

*Female parent.*—Proprietary *Calibrachoa×hybrida* breeding selection designated 2087-1, not patented.

*Male parent.*—Proprietary *Calibrachoa×hybrida* breeding selection designated 2080-1A, not patented.

Propagation:

*Type cutting.*—Terminal stem.

*Time to initiate roots.*—Approximately 6 to 8 days.

*Time to produce a rooted cutting.*—Approximately 24 to 28 days.

*Root description.*—Fibrous.

*Rooting habit.*—Freely branching.

Plant description:

*Commercial crop time.*—Approximately 6 to 7 weeks from a rooted cutting.

*Growth habit and general appearance.*—Moderately vigorous and trailing, becoming mounded with age.

*Size.*—Height from soil level to top of plant plane: Approximately 14.8 cm. Width: Approximately 56.5 cm.

*Branching habit.*—Freely branching. Quantity of main branches per plant: Approximately 5.

*Branch.*—Strength: Strong. Length: Approximately 35.1 cm. Diameter: Approximately 3.0 mm. Length of central internode: Approximately 1.9 cm. Texture: Densely glandular pubescent. Color of young stem: 144B. Color of mature stem: 144B with overlay of 187B on upward facing surface.

Foliage description:

*General description.*—Quantity of leaves per main branch: Approximately 45. Fragrance: Slight. Form: Simple. Arrangement on flowering stem: Opposite.

*Leaves.*—Aspect: At acute angle to stem with tip turning downward. Shape: Elliptic. Margin: Entire. Apex: Obtuse. Base: Attenuate. Venation pattern: Pinnate. Length of mature leaf: Approximately 3.1 cm. Width of mature leaf: Approximately 1.1 cm. Texture of upper and lower surfaces: Glandular pubescent. Color of upper surface of young foliage: 137C with venation of 144D. Color of lower surface of young foliage: 138C with venation of 144D. Color of upper surface of mature foliage: 137A with venation of 144D. Color of lower surface of mature foliage: 138B with venation of 144D.

*Petiole.*—Length: Approximately 7.5 mm. Diameter: Approximately 1.0 mm. Texture: Glandular pubescent. Color: 144D.

Flowering description:

*Flowering habit.*—'Balcablitpi' is freely flowering under outdoor growing conditions with substantially continuous blooming from spring through autumn and year-round in greenhouse environment.

*Lastingness of individual flower on the plant.*—Approximately 9 to 11 days.

Flower description:

*General description.*—Type: Single, salverform. Quantity per plant: Approximately 31. Fragrance: None.

*Bud.*—Rate of opening: Generally takes 3 to 4 days for bud to progress from first color to fully open flower. Quantity per plant: Approximately 5.

*Bud just before opening.*—Shape: Oblong. Length: Approximately 1.9 cm. Diameter: Approximately 4.6 mm. Texture: Densely glandular pubescent. Color: Petals of 76C and corolla tube of 145C, both with venation of N144D having an overlay of N186C.

*Corolla.*—Diameter: Approximately 3.2 cm.

*Petals.*—Quantity: 5, fused to form a tube. Shape: Obovate. Margin: Entire. Apex: Obtuse. Length from tube: Approximately 1.4 cm. Length of free portion: Approximately 6.7 mm. Width: Approximately 1.5 cm. Texture of upper surface: Glabrous. Texture of lower surface: Glandular pubescent, dense along the veins. Color of upper surface when first open: N74B with midveins of N186C. Color of lower surface when first open: 76D with midveins of 144D having a faint overlay of N186C. Color of upper surface when fully open: N74C with base of N74B and midveins of N186C. Color of lower surface when fully open: 76D with midveins of 144D having a faint overlay of N186C.

*Corolla tube.*—Length: Approximately 1.6 cm. Diameter at distal end: Approximately 7.4 mm. Diameter at proximal end: Approximately 2.0 mm. Texture of inner surface: Glabrous. Texture of outer surface: Glandular pubescent. Color of inner surface: 12B with venation of N186C. Color of outer surface: 145C with venation of 144C having a faint overlay of N186C.

*Peduncle.*—Strength: Strong. Aspect: Acute angle to stem. Length: Approximately 1.3 cm. Diameter: Approximately 1.0 mm. Texture: Densely glandular pubescent. Color: 144B.

*Sepals.*—Quantity per flower: 5, fused along lower half. Shape: Lanceolate. Apex: Acute. Length: Approximately 1.1 cm. Width: Approximately 2.0 mm. Texture of upper and lower surfaces: Densely glandular pubescent. Color of upper surface: 137B. Color of lower surface: 137B with 144B at base.

*Reproductive organs.*—Androecium: Stamen quantity: 5 per flower, fused to inside of corolla tube. Stamen length: Approximately 8.5 mm. Filament length of free portion: Approximately 4.8 mm. Filament color: 144D. Anther shape: 2 parted, oval. Anther length: Approximately 1.0 mm. Anther color: 8A. Pollen amount: Abundant. Pollen color: 8C. Gynoecium: Pistil quantity: 1 per flower. Pistil length: Approximately 9.2 mm. Stigma shape: Funnel. Stigma length: Approximately 1.0 mm. Stigma color: 143A. Style length: Approximately 6.2 mm. Style color: 144D. Ovary diameter: Approximately 2.0 mm. Ovary color: 144A.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcablitpi', substantially as herein shown and described.

* * * * *